United States Patent
Romuald

(10) Patent No.: US 10,028,815 B2
(45) Date of Patent: Jul. 24, 2018

(54) PROSTHESIS WITH ZIGZAG SEAM

(75) Inventor: Gaëtan Romuald, Bron (FR)

(73) Assignee: Sofradim Production, Trevoux (FR)

( * ) Notice: Subject to any disclaimer, the term of this patent is extended or adjusted under 35 U.S.C. 154(b) by 183 days.

(21) Appl. No.: 13/990,047

(22) PCT Filed: Dec. 9, 2011

(86) PCT No.: PCT/EP2011/072384
§ 371 (c)(1),
(2), (4) Date: Jul. 15, 2013

(87) PCT Pub. No.: WO2012/076712
PCT Pub. Date: Jun. 14, 2012

(65) Prior Publication Data
US 2013/0296898 A1    Nov. 7, 2013

(30) Foreign Application Priority Data
Dec. 9, 2010 (FR) ...................... 10 60287

(51) Int. Cl.
*A61F 2/00* (2006.01)

(52) U.S. Cl.
CPC .......... *A61F 2/0063* (2013.01); *A61F 2/0045* (2013.01); *A61F 2210/0004* (2013.01); *A61F 2250/0097* (2013.01)

(58) Field of Classification Search
CPC ................... A61F 2/0063; A61F 2/105; A61F 2250/0097; A61F 2002/0068; A61F 2/04–2002/077; D10B 2509/08
USPC ..... 606/151; 623/23.74, 23.72, 13.11, 13.19, 623/13.2; 112/157; 600/37
See application file for complete search history.

(56) References Cited

U.S. PATENT DOCUMENTS

| | | | | |
|---|---|---|---|---|
| 2,808,267 A | * | 10/1957 | Heaton | .......................... 473/212 |
| 5,025,740 A | * | 6/1991 | Horie | ................... D05B 19/105 |
| | | | | 112/456 |
| 5,061,283 A | * | 10/1991 | Silvestrini | ..................... 128/898 |

(Continued)

FOREIGN PATENT DOCUMENTS

| | | |
|---|---|---|
| FR | 2194406 | 3/1974 |
| WO | WO 83/03347 | 10/1983 |
| WO | 03037217215 A2 | 5/2003 |

OTHER PUBLICATIONS

Making Machine Stitches Work for You. Dec. 24, 2008. Accessed Apr. 16, 2015. <http://www.dummies.com/how-to/content/making-machine-stitches-work-for-you.html>.*

(Continued)

*Primary Examiner* — Ryan J Severson
*Assistant Examiner* — Charles Wei

(57) ABSTRACT

The present invention relates to a prosthesis (1) intended to be implanted at an implantation site, comprising means of information (5) intended to guide the surgeon for performing the implantation of the prosthesis according to a defined arrangement, said prosthesis comprising at least one porous textile (2) having two faces (3,4) separated by a certain thickness, said means of information comprising at least one seam (5) provided in said textile, said seam traversing the thickness of said textile from one face to the other of said textile while preserving said thickness of said textile, said seam defining a zigzag pattern on at least one face of the textile.

16 Claims, 2 Drawing Sheets

(56) References Cited

U.S. PATENT DOCUMENTS

| | | | |
|---|---|---|---|
| 5,254,133 A * | 10/1993 | Seid | A61B 17/0057 128/899 |
| 6,066,776 A * | 5/2000 | Goodwin | A61F 2/0063 606/151 |
| 6,214,029 B1 * | 4/2001 | Thill | A61B 17/0057 606/213 |
| 6,391,060 B1 * | 5/2002 | Ory | A61F 2/0063 606/151 |
| 6,840,962 B1 * | 1/2005 | Vacanti et al. | 623/23.76 |
| 8,298,286 B2 * | 10/2012 | Trieu | A61B 17/8085 623/17.11 |
| 8,906,045 B2 * | 12/2014 | Levin | A61B 17/00491 606/151 |
| 2002/0189622 A1 * | 12/2002 | Cauthen, III | A61F 2/441 128/898 |
| 2003/0004581 A1 * | 1/2003 | Rousseau | A61F 2/0063 623/23.74 |
| 2003/0074100 A1 * | 4/2003 | Kaymer | D05B 19/08 700/138 |
| 2003/0192561 A1 * | 10/2003 | Murphy | A61B 17/0218 128/898 |
| 2005/0070829 A1 * | 3/2005 | Therin | A61F 2/0045 602/1 |
| 2005/0261782 A1 * | 11/2005 | Hoganson | A61F 2/0063 623/23.74 |
| 2005/0288691 A1 * | 12/2005 | Leiboff | A61F 2/0063 606/151 |
| 2006/0253203 A1 * | 11/2006 | Alvarado | 623/23.74 |
| 2007/0079846 A1 * | 4/2007 | Keating | A45D 8/26 132/278 |
| 2008/0167729 A1 | 7/2008 | Nelson et al. | |
| 2009/0036907 A1 * | 2/2009 | Bayon et al. | 606/151 |
| 2009/0319053 A1 | 12/2009 | Chu | |
| 2010/0189764 A1 * | 7/2010 | Thomas | A61F 2/0063 424/426 |
| 2011/0082478 A1 * | 4/2011 | Glick | A61B 17/06166 606/148 |
| 2011/0184440 A1 * | 7/2011 | Saldinger | A61F 2/0063 606/151 |
| 2011/0184441 A1 * | 7/2011 | St-Germain | A61F 2/0063 606/151 |
| 2011/0287904 A1 * | 11/2011 | Morris | A63B 21/0602 482/93 |
| 2012/0232334 A1 * | 9/2012 | Bell | A61M 39/0613 600/37 |

OTHER PUBLICATIONS

PCT Search Report for corresponding PCTEP2011/072384, dated Jan. 20, 2012 (4 pgs).

* cited by examiner

PROSTHESIS WITH ZIGZAG SEAM

The present invention relates to a prosthesis based on a textile and comprising means for informing the surgeon, for the purpose of promoting implantation of the prosthesis according to a defined disposition.

Many prostheses, for example abdominal wall reinforcements or bands for treating urinary incontinence, are in the form of a piece of biocompatible textile, which may or may not be accompanied by additional elements, for example a coating in the form of a film, reinforcing elements, a set of needles, etc. The textile piece of these prostheses can be either symmetric or asymmetric. This is notably the case with prostheses for wall reinforcement, for example of the abdominal wall, which are widely used in surgery and are intended for treating hernias by filling a tissue defect, temporarily or permanently. These prostheses can have various shapes, rectangular, circular, oval, and preferably also show some elasticity in various directions, depending on the anatomical structure to which they must be adapted. Some of these prostheses are performed using threads that are entirely biodegradable and are intended to disappear after they have provided their function of reinforcement while cellular colonization takes place and tissue rehabitation takes over. Others comprise non-biodegradable threads and are intended to remain in the patient's body permanently.

In any case, for reasons of safety, these prostheses must often be arranged in a specific manner, very precisely in relation to the surrounding organs at the moment of implantation. Thus, it is sometimes necessary to provide these prostheses with markers or means of information, intended to give the surgeon information about the particular properties of one face of the textile or about the dimensions or about the location of a precise point of the piece of textile, or about the position that a particular form of the prosthesis must occupy.

Thus, depending on the environment of the implantation site, for example the presence of internal organs, soft tissues, etc., it may be important to provide the surgeon with information about a given place of the textile, so that the surgeon can ensure that the piece of textile is positioned in a particular orientation or to position a certain region of the prosthesis opposite a particular organ or conversely as far away from a particular organ as possible, and so on.

Prostheses based on a textile comprising markers or means of information already exist.

One solution for providing prostheses with markers is to provide marking based on additional threads that are added to the basic textile.

For example, they can be embroidered with suture threads: however, such a solution is tedious and time-consuming for providing the embroidery. Moreover, adding embroidery to a textile causes distortion of said textile and excesses of neofibrosis may appear depending on the density of the embroidery applied.

Moreover, embroidery may alter the essential properties of the basic textile. Thus, when the basic textile has a certain elasticity, necessary for the function that the prosthesis is to perform, embroidery has the drawback of blocking the textile, causing it to lose its elasticity. Moreover, when the textile has a certain thickness, the embroidery or seams of the prior art also have the drawback of changing the thickness of the textile, making the textile unsuitable for certain applications.

Thus, there is a need to be able to provide the textile of a prosthesis with means of information reliably and quickly without affecting the properties, in particular thickness and elasticity, of the prosthesis itself.

The present invention aims to meet this need by supplying a prosthesis based on a textile, provided with means of information in the form of at least one particular seam, said seam not having any adverse effect on the properties of the prosthesis and on its effectiveness.

A first aspect of the present invention is a prosthesis intended to be implanted at an implantation site, comprising means of information intended to guide the surgeon for performing the implantation of the prosthesis according to a defined arrangement, said prosthesis comprising at least one porous textile having two faces separated by a certain thickness, said means of information comprising at least one seam incorporated in said textile, said seam traversing the thickness of said textile from one face to the other of said textile while preserving said thickness of said textile, said seam defining a zigzag pattern on at least one face of the textile.

"Seam defining a zigzag pattern" means, according to the present application, that the seam follows a path formed by a succession of broken lines forming salient and reentrant angles alternately.

The particular form of the seam of the prosthesis according to the invention makes it possible to preserve the properties of the prosthesis. In particular, if the textile of the prosthesis according to the invention has a certain elasticity, the particular form of the seam makes it possible for this elasticity to be substantially preserved. The properties of the textile are not affected by the presence of the zigzag seam. In particular, the zigzag seam does not block the textile. In particular, the porosity of the textile of the prosthesis of the invention is maintained even in the presence of one or more zigzag seams. Moreover, the particular form of the seam of the prosthesis according to the invention makes it possible to preserve the initial thickness of the textile: in fact, as will be clear from the description given below, the thread or threads forming the seam traverse the thickness of the textile without crushing the textile, as the height of the seam corresponds to the thickness of the textile.

"Textile" means, in the sense of the present application, any textile obtained by an arrangement or assemblage of biocompatible yarns, threads, fibres, monofilaments and/or multifilaments, such as knitting, weaving, braiding and/or non-woven and having two opposite faces. The textile of the prosthesis according to the invention has a certain thickness—the thickness separating its two opposite faces.

The yarns, threads, or fibres or filaments and/or multifilaments forming the textile according to the invention can be made of any biocompatible material, whether or not biodegradable.

"Biodegradable" or "bioabsorbable" means, in the sense of the present application, the characteristic according to which a material is absorbed and degraded by biological tissues and disappears in vivo after a certain period, which can vary for example from some hours to some months, depending on the chemical nature of the material.

Thus, biodegradable materials suitable for the yarns or threads of the textile of the present invention can be selected from poly(lactic) acid (PLA), poly(glycolic) acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof. Non-biodegradable materials suitable for the yarns or threads of the textile of the present invention can be selected from polyethylene terephthalate (PET), polyamides, aramids, expanded polytetrafluoroethylene, polyurethane, polyvinylidene difluoride (PVDF), polybutyl esters, PEEK (polyetheretherketone), polyolefins (such as polyethylene or polypropylene), copper alloys, silver alloys, platinum alloys, medical grades of steel such as medical-grade stainless steel, and combinations thereof.

In one embodiment of the invention, said seam also defines a zigzag pattern on the second face of the textile.

In one embodiment of the invention, said means of information comprise a plurality of seams defining a zigzag pattern, arranged at specific places of said textile.

Thus, a zigzag seam of the prosthesis according to the invention can indicate a precise point of the textile, depending on the shape of the latter, such as its centre, or conversely a point situated at a certain distance from the centre or from the edge, etc. Alternatively or in combination, a seam can simply indicate a particular face of the textile, for example an openwork face, as opposed for example to a face sealed by a post-surgical anti-adhesion film. A seam can also indicate the side by which the prosthesis must be introduced. For example, if the prosthesis must be folded on itself for introduction at the implantation site, a seam can indicate the place or line along which the prosthesis must be folded, etc.

In one embodiment of the invention, the textile is a knitted fabric. Knitted fabric means, according to the present application, an arrangement of threads obtained by knitting. The knitted fabric can be two-dimensional or three-dimensional.

Two-dimensional knitted fabric means, in the sense of the present application, a knitted fabric having two opposite faces joined together by stitches but lacking an intermediate binding layer: a knitted fabric of this kind can be obtained for example by knitting threads on a warp knitting machine or Raschel machine by means of two guide bars. Examples of knitting of two-dimensional knitted fabrics suitable for the present invention are given in document WO2009/071998.

Three-dimensional knitted fabric means, according to the present application, a knitted fabric having two opposite faces joined together by an intermediate binding layer, said intermediate binding layer itself being formed of additional linking threads in addition to the threads forming the two faces of the knitted fabric. A knitted fabric of this kind can for example be obtained with a warp knitting machine or Raschel machine with double needle bed using several guide bars. Examples of knitting of three-dimensional knitted fabrics suitable for the present invention are given in documents WO99/05990, WO2009/031035, WO2009/071998. In particular, three-dimensional knitted fabrics show an adequate elasticity for prostheses of the invention intended to be used as wall reinforcement.

As a porous textile, the textile of the prosthesis according to the invention has both its faces as openwork. "Openwork face" means, according to the present application, that the face of the textile comprises openings, gaps, pores or spaces, open towards the exterior. These openings promote penetration of cells into the textile and therefore cellular recolonization of the prosthesis after implantation.

The seam of the prosthesis according to the invention, because of its zigzag form, does not alter the ability of the openwork faces of the textile to promote cellular recolonization.

The textile of the invention is a porous textile, for example a porous knitted fabric: this means, according to the present application, that the textile of the invention has gaps, pores or spaces, not only at its faces but also in its thickness. Said gaps, pores or spaces can constitute channels opening onto either side of the textile. A porous textile of this kind permits better tissue integration, as the cells can reach the interior of the textile forming the reinforcement of the abdominal wall, for example. In addition, the porosity of the textile of the prosthesis of the invention confers to said textile an elasticity allowing said prosthesis to adapt to the anatomical structure it is intended to reinforce, such as an abdominal wall for example.

For example, the weave of the textile of the invention, and in particular of the knitted fabric, can produce, in the thickness of said textile, a multiplicity of gaps or transverse channels, roughly parallel to one another, opening on either side of said textile on its two openwork faces respectively, for example endowing the textile with a "honeycomb" structure.

Examples of porous three dimensional knitted fabrics suitable for the textile of the prosthesis of the invention and showing in the thickness of the knitted fabric such transverse channels, roughly parallel to one another, opening on either side of the knitted fabric on its two openwork faces respectively, may be obtained by knitting yarns, for example polyethylene terephthalate multifilaments yarns, on a Raschel loom with six guide bars B1-B6 according to the following weave pattern, expressed according to standard ISO 11676:

B1: 1.2.1.1/1.0.1.1/1.2.1.1/1.0.1.1/1.2.2.2/3.2.2.2/1.2.2.2/3.2.2.2//

B2: 1.2.2.2/3.2.2.2/1.2.2.2/3.2.2.2/1.2.1.1/1.0.1.1/1.2.1.1/1.0.1.1//

B3: 0.1.0.1/0.0.0.0//

B4: 0.1.0.1/0.0.0.0//

B5: 1.1.0.1/1.1.2.1/1.1.0.1/1.1.2.1/2.2.2.3/2.2.2.1/2.2.2.3/2.2.2.1//

B6: 2.2.2.3/2.2.2.1/2.2.2.3/2.2.2.1/1.1.0.1/1.1.2.1/1.1.0.1/1.1.2.1//

Alternatively, the weave pattern may be the following one, expressed according to standard ISO 11676:

B1: 1.0.1.1/1.2.1.1/1.0.1.1/2.3.2.2/2.1.2.2/2.3.3.3/4.5.4.4/4.3.4.4/4.5. 4.4/3.2.3.3/3.4.3.3/3.2.2.2//

B2: 4.5.4.4/4.3.4.4/4.5.4.4/3.2.3.3/3.4.3.3/3.2.2.2/1.0.1.1/1.2.1.1/1.0. 1.1/2.3.2.2/2.1.2.2/2.3.3.3//

B3: 1.1.1.0/1.0.1.0/1.0.1.1/1.1.1.0/2.3.2.3/2.3.2.2/2.2.2.3/2.3.2.3/2.3. 2.2/2.2.2.3/1.0.1.0/1.0.1.1//

B4: 2.2.2.3/2.3.2.3/2.3.2.2/2.2.2.3/1.0.1.0/1.0.1.1/1.1.1.0/1.0.1.0/1.0. 1.1/1.1.1.0/2.3.2.3/2.3.2.2//

B5: 2.2.1.0/1.1.1.2/1.1.1.0/1.1.2.3/2.2.2.1/2.2.2.3/3.3.4.5/4.4.3/4.4. 4.5/4.4.3.2/3.3.3.4/3.3.3.2//

B6: 3.3.4.5/4.4.4.3/4.4.4.5/4.4.3.2/3.3.3.4/3.3.3.2/2.2.1.0/1.1.1.2/1.1. 1.0/1.1.2.3/2.2.2.1/2.2.2.3//

The seam of the prosthesis according to the invention, because of its height, corresponding to the thickness of the textile, does not alter the ability of the pores present in the thickness of the textile to promote cellular recolonization.

The seam or seams of the prosthesis according to the invention can be made of any biocompatible thread. The threads, or fibres or filaments and/or multifilaments forming the seam of the textile of the prosthesis according to the invention can be made of any biocompatible material, whether or not biodegradable, as defined above for the textile. These threads can for example be braided together and can be in the form of a braid.

In one embodiment of the prosthesis, the zigzag seam is produced from coloured biocompatible threads.

Thus, the seams of the prosthesis according to the invention can be produced from threads that are coloured intrinsically, i.e. coloured naturally without deposition of an ink that is unfavourable to cellular colonization. In particular, it is possible to make the seams using coloured suture threads that are recognized as biocompatible by the current regulations for medical devices. Such threads suitable for making the seams of the prosthesis according to the invention are for example the braids of polyester threads coloured green, marketed under the designation "EP 1.0 D&C No. 6 Green Polyester Wax" by the company Pearsalls Ltd.

With this embodiment it is possible to produce a prosthesis according to the invention particularly simply and quickly. In fact, the textile of the prosthesis has not undergone any special treatment for colouring certain of its parts with the risks of infection, distortion or damage that this involves. It is sufficient to provide the textile with one or more zigzag seams made from coloured threads, said seams being arranged in order to give particular information to the surgeon, the colour difference between the textile and the seams being effective for attracting the surgeon's attention.

Thus, the prosthesis according to the invention, although equipped with means of information, does not lose the initial properties of the basic textile. In particular, the elasticity and thickness of the basic textile of the prosthesis according to the invention are substantially preserved. The porosity of the textile of the prosthesis according to the invention is also preserved.

In one embodiment of the invention, said seams are produced from biodegradable material, a s defined above. Examples of biodegradable materials suitable for the threads for the seam or seams of the prosthesis according to the invention are polylactic acid (PLA), copolymer of glycolic acid and lactic acid (GLA), polydioxanone and mixtures thereof.

Said embodiment offers the advantage of supplying useful information to the surgeon at the moment of implantation of the prosthesis, without burdening the patient with the presence of an amount of foreign bodies that is too great in the long term, as the seam or seams are absorbed and disappear after a certain period following implantation.

The advantages of the present invention will become clearer on reading the description and example that follow and from the appended drawings in which.

Figure 1:
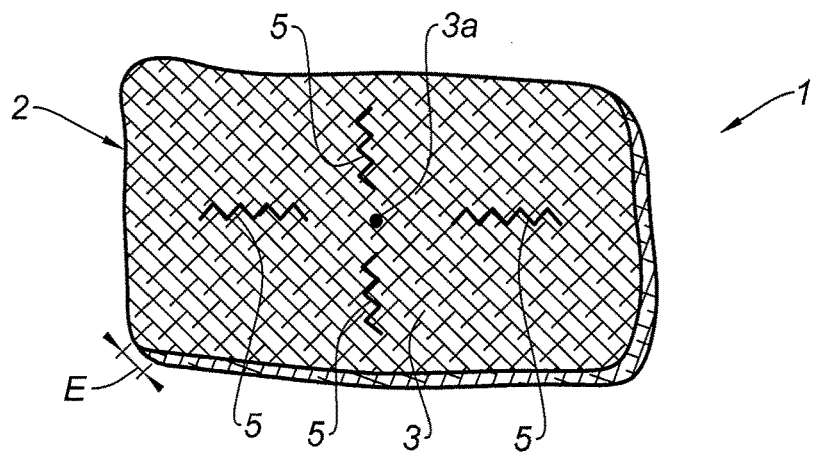
FIG. 1 is a perspective top view of a prosthesis according to the invention
Figure 2:
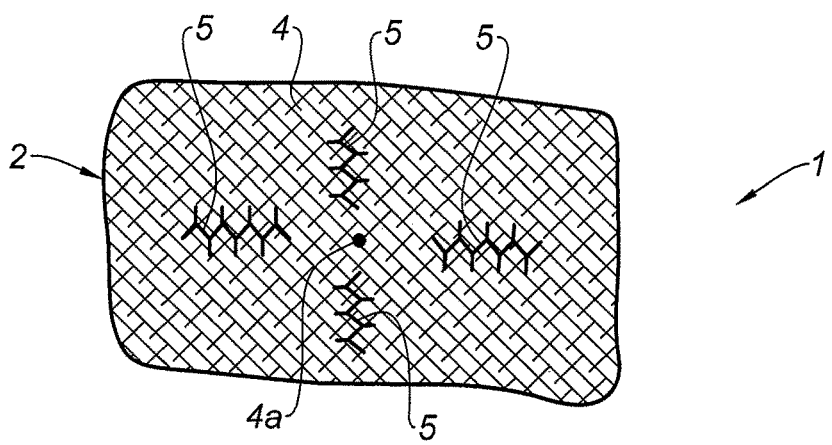
FIG. 2 is a view of the prosthesis of FIG. 1 from underneath.

Referring to FIGS. 1 and 2, a prosthesis according to the present invention is represented generally by reference 1, viewed from above (FIG. 1) and viewed from underneath (FIG. 2). The prosthesis 1 comprises a textile in the form of a piece of textile 2 of overall rectangular shape and having a thickness E. Said piece of textile 2 can advantageously be used for repairing an abdominal wall hernia. Referring to FIGS. 1 and 2, the piece of textile 2 has two opposite faces 3 and 4. These two faces can be of openwork.

Said textile can be obtained by the methods described in documents WO99/05990, WO2009/031035, WO2009/071998.

In the example shown in FIGS. 1 and 2, the textile 2 is provided with four seams 5.

Figure 3:
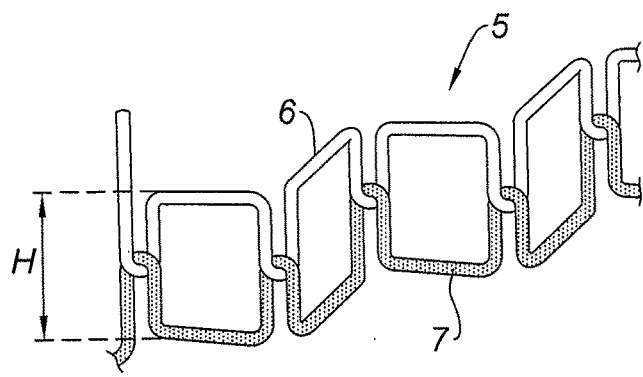
FIG. 3 is a schematic perspective view of a seam of the prosthesis of FIGS. 1 and 2

The seams 5 are produced on the textile 2 on a tied-stitch machine producing a zigzag pattern. The pattern is formed by interlacing a loop of a needle thread 6 and of a bobbin thread 7, as shown in FIG. 3, which shows a single seam 5 schematically in perspective. The threads (6, 7) forming the seams 5 are for example coloured biocompatible threads such as suture braids of polyester coloured green, sold under the trade name "EP 1.0 D&C No. 6 Green Polyester Wax" by the company Pearsalls Ltd.

The needle thread 6 and bobbin thread 7 can be identical or different.

As can be seen from FIG. 3, the seam 5 has a certain height H. This height H corresponds to the thickness E of the textile 2; this makes it possible to preserve the thickness of the textile 2 at the location of the seams 5.

As can be seen from FIGS. 1 and 2, the seams 5 traverse the thickness of the textile 2 and they each define a zigzag pattern on each of the faces (3, 4) of the textile 2: thus, each seam follows a path formed by a succession of broken lines forming salient and reentrant angles alternately, on each face (3, 4) of the textile 2. The four seams 5 make it possible in particular, in the example shown, for the centre (3*a*, 4*a*) of each face (3, 4) of the textile 2 to be located easily.

Owing to their zigzag shape, the seams 5 of the prosthesis according to the invention allow the elasticity of the textile 2 to be preserved.

Owing to their colour, different from that of the basic textile, the seams are immediately visible and can easily be interpreted by the surgeon.

EXAMPLE

A knitted fabric has been prepared on a Raschel loom with six guide bars B1-B6 according to the following weave pattern, expressed according to standard ISO 11676:

B1: 1.2.1.1/1.0.1.1/1.2.1.1/1.0.1.1/1.2.2.2/3.2.2.2/1.2.2.2/3.2.2.2//

B2: 1.2.2.2/3.2.2.2/1.2.2.2/3.2.2.2/1.2.1.1/1.0.1.1/1.2.1.1/1.0.1.1//

B3: 0.1.0.1/0.0.0.0//

B4: 0.1.0.1/0.0.0.0//

B5: 1.1.0.1/1.1.2.1/1.1.0.1/1.1.2.1/2.2.2.3/2.2.2.1/2.2.2.3/2.2.2.1//

B6: 2.2.2.3/2.2.2.1/2.2.2.3/2.2.2.1/1.1.0.1/1.1.2.1/1.1.0.1/1.1.2.1//

The guide bars were threaded 1 in, 1 out with white polyethylene terephthalate (PET) multifilament yarns.

A three-dimensional knitted fabric having two opposite faces, separated by the thickness of the knitted fabric, and joined together by an intermediate binding layer, is obtained. The obtained knitted fabric is porous, i.e. has gaps, pores or spaces, not only at its faces, but also in its thickness. In particular, the above weave pattern produces, in the thickness of the knitted fabric, a multiplicity of gaps or transverse channels, roughly parallel to one another, opening on either side of the knitted fabric on its two openwork faces respectively. The obtained knitted fabric also shows an elasticity (see measures below) allowing it to adapt to an anatomical structure such as an abdominal wall.

The following samples are prepared from this knitted fabric:

Sample A: control sample on which no seam is performed

Sample B: a zigzag seam is performed following a global direction that is perpendicular to the warp direction of the knitted fabric, Sample C: a zigzag seam is performed following a global direction that is parallel to the warp direction of the knitted fabric, Sample D: a straight seam is performed along a line that is perpendicular to the warp direction of the knitted fabric, Sample E: a straight seam is performed along a line that is parallel to the warp direction of the knitted fabric.

The zigzag seams of samples B and C are performed as explained above with reference to FIG. 3, on a tied-stitch machine producing a zigzag pattern, by interlacing a loop of a needle thread and of a bobbin thread. The zigzag seam has a height corresponding to the thickness of the knitted fabric, as shown on FIG. 3: the knitted fabric is therefore not flattened by the presence of the zigzag seam and its thickness is maintained.

The straight seams of samples D and E are performed according to a classic method for producing a straight seam.

The thread used for performing the seams of samples B, C D and E is a suture braid of polyester coloured green, sold under the trade name "EP 1.0 D&C No. 6 Green Polyester Wax" by the company Pearsalls Ltd.

Samples B and C are therefore textiles suitable for the present invention. Samples A, D and E are comparative textiles.

The elasticity has been measured for samples A-E by measuring the breaking strength and elongation for each sample according to the testing method described in standard ISO 13934-1: 1999 "Determination of Breaking strength and elongation" with the following conditions:

Length between jaws: 200 mm
Crosshead speed: 100 mm/min
Pre-load: 2 N

The test is performed on 5 exemplaries for each sample.

Figure 4:
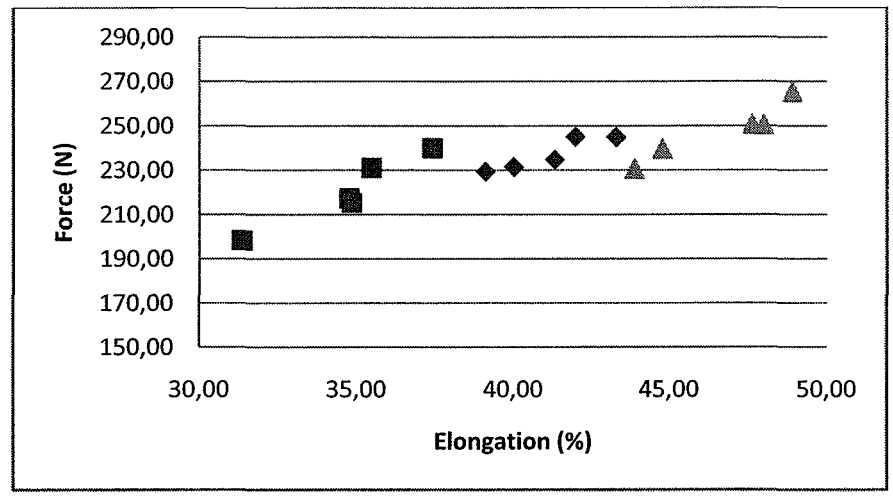
FIG. 4 is a graphic showing the breaking strength (force) in function of the elongation for a knitted fabric with a zigzag seam according to the invention and two comparative fabrics.

On FIG. 4 are shown the results obtained for samples A, B and D: FIG. 4 is a graphic showing the force (breaking strength) in function of the elongation (%), for samples A, B and D, with the following designations:

▲Sample A (control: no seam)
♦Sample B (ZigZag seam according to the invention)
■Sample D (Straight seam: comparative)

As can be seen from FIG. 4, the textile according to the invention, with a zigzag seam (sample B) maintains the elasticity of the knitted fabric. Indeed, with reference to this Figure, it can be seen that the knitted fabric with no seam (sample A) shows an elasticity corresponding to an elongation varying from 43% to 49%, for a force varying from 230 N to 266 N. The knitted fabric according to the invention (sample B) shows an elasticity corresponding to an elongation varying from 39% to 44%, for a force varying from 229 N to 245 N, whereas the comparative knitted fabric (sample D) shows an elasticity corresponding to an elongation varying from 31% to 38%, for a force varying from 198 N to 240 N.

Figure 5:
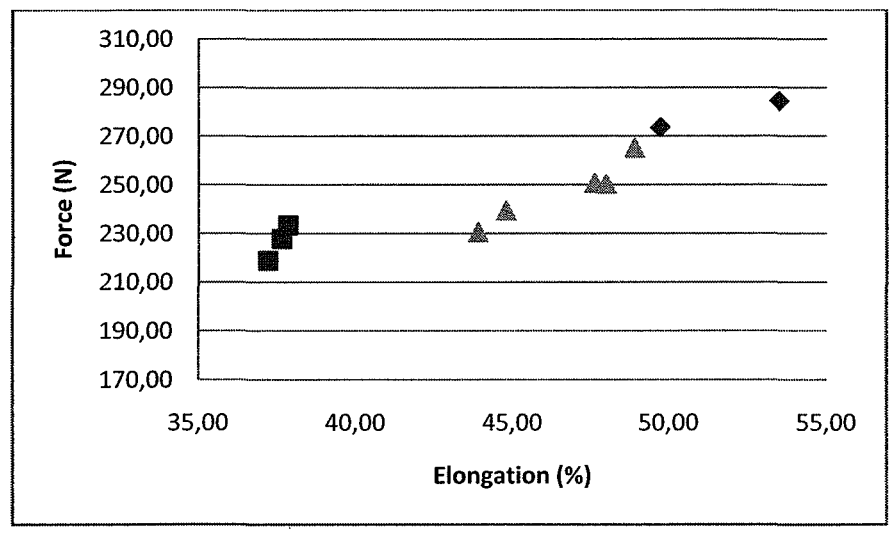
FIG. 5 is a graphic showing the breaking strength (force) in function of the elongation for another knitted fabric with a zigzag seam according to the invention and two comparative fabrics.

On FIG. 5 are shown the results obtained for samples A, C and E: FIG. 5 is a graphic showing the force (breaking strength) in function of the elongation (%), for samples A, C and E, with the following designations:

▲Sample A (control: no seam)
♦Sample C (ZigZag seam according to the invention)
■Sample E (Straight seam: comparative)

As can be seen from FIG. 5, the textile according to the invention, with a zigzag seam (sample C) not only maintains the elasticity of the knitted fabric but improves said elasticity, by comparison with the knitted fabric with no seam (sample A). Indeed, with reference to this Figure, it can be seen that the knitted fabric with no seam (sample A) shows an elasticity corresponding to an elongation varying from 43% to 49%, for a force varying from 230 N to 266 N. The knitted fabric according to the invention (sample C) shows an elasticity corresponding to an elongation varying from 63% to 69%, for a force varying from 273 N to 285 N, whereas the comparative knitted fabric (sample E) shows an elasticity corresponding to an elongation varying from 37% to 38%, for a force varying from 1218 N to 234 N.

It is therefore possible to manufacture a prosthesis according to the invention with one or more seams defining a zigzag pattern, from knitted fabrics of samples B and C, the elasticity of the knitted fabric being maintained when said zigzag seams are added, said elasticity allowing the prosthesis to adapt to the anatomical structure it is intended to reinforce, such as an abdominal wall.

The invention claimed is:

1. A prosthesis intended to be implanted at an implantation site comprising a three-dimensional knit fabric having a first face and a second face opposite the first face, the first face and the second face being separated by a thickness of the knit fabric, the knit fabric including pores on the first face, the second face and the thickness of the knit fabric, and a plurality of separate, distinct, and non-overlapping seams configured to locate a first center on the first face of the fabric and a second center on the second face of the fabric, each seam of the plurality of seams defining a zigzag pattern on both the first and second faces of the knit fabric, wherein the first center on the first face and the second center on the second face are positioned between the plurality of seams and free of the plurality of seams, wherein a global direction of a first seam of the plurality of seams is perpendicular to a global direction of a second seam of the plurality of seams.

2. The prosthesis of claim 1, wherein each seam is formed from biocompatible colored threads.

3. The prosthesis of claim 2, wherein each seam is formed from threads of biodegradable material.

4. The prosthesis of claim 1, wherein the pores comprise transverse channels, roughly parallel to one another, opening on either face of said fabric.

5. The prosthesis of claim 1, wherein at least one seam of the plurality of seams follows a global direction that is parallel to a warp direction of the knit fabric.

6. The prosthesis of claim 5, wherein at least one seam of the plurality of seams follows a global direction that is perpendicular to the warp direction of the knit fabric.

7. The prosthesis of claim 6, wherein the plurality of seams comprises four seams.

8. The prosthesis of claim 7, wherein two of the four seams follow a global direction that is parallel to the warp direction of the knit fabric and two of the four seams follow a global direction that is perpendicular to the warp direction of the knit fabric.

9. The prosthesis of claim 1, wherein the knit fabric includes an elasticity and the plurality of seams maintains the elasticity of the knit fabric.

10. The prosthesis of claim 1, wherein the plurality of seams does not alter the ability of the pores of the knit fabric to promote cellular recolonization.

11. The prosthesis of claim 1, wherein the knit fabric comprises polyethylene terephthalate yarns.

12. The prosthesis of claim 11, wherein the plurality of seams comprises colored polyester yarns.

13. The prosthesis of claim 1, wherein each seam of the plurality of seams traverses the thickness of said fabric from one face to the other of said fabric while preserving said thickness of said fabric.

14. The prosthesis of claim 13, wherein a height of each seam of the plurality of seams corresponds to the thickness of the knit fabric.

15. The prosthesis of claim 1, wherein the prosthesis is a hernia repair device.

16. A prosthesis intended to be implanted at an implantation site comprising a three-dimensional knit fabric having a first face and a second face opposite the first face, the first face and the second face being separated by a thickness of the knit fabric, the knit fabric including pores on the first face, the second face and the thickness of the knit fabric, and a plurality of separate, distinct, and non-overlapping seams configured to locate a first center on the first face of the fabric and a second center on the second face of the fabric, each seam of the plurality of seams defining a zigzag pattern on at least the first face of the knit fabric, wherein the first center on the first face and the second center on the second face are positioned between the plurality of seams and free of the plurality of seams, wherein a global direction of a first seam of the plurality of seams is perpendicular to a global direction of a second seam of the plurality of seams.

\* \* \* \* \*